(12) United States Patent
Gutman et al.

(10) Patent No.: US 7,696,356 B2
(45) Date of Patent: Apr. 13, 2010

(54) PROCESS FOR PREPARING 1,2,3,9-TETRAHYDRO-9-METHYL-3-METHYLENE-4H-CARBAZOL-4-ONE AND ONDANSETRON THEREFROM

(75) Inventors: Daniella Gutman, Rishon Lezion (IL); Rosa Cyjon, Haifa (IL)

(73) Assignee: Taro Pharmaceutical Industries Limited, Haifa Bay (IL)

( * ) Notice: Subject to any disclaimer, the term of this patent is extended or adjusted under 35 U.S.C. 154(b) by 1184 days.

(21) Appl. No.: 11/204,539

(22) Filed: Aug. 16, 2005

(65) Prior Publication Data

US 2006/0041004 A1 Feb. 23, 2006

Related U.S. Application Data

(60) Provisional application No. 60/602,141, filed on Aug. 17, 2004.

(51) Int. Cl.
*C07D 209/88* (2006.01)
*C07D 403/06* (2006.01)

(52) U.S. Cl. .................... 548/311.4; 548/439

(58) Field of Classification Search .............. 548/311.4, 548/440
See application file for complete search history.

(56) References Cited

U.S. PATENT DOCUMENTS

| 4,104,462 | A | * | 8/1978 | Fischer et al. ............. 536/27.22 |
| 4,298,615 | A | * | 11/1981 | Schwarz et al. ............. 514/469 |
| 4,695,578 | A | | 9/1987 | Coates et al. |
| 4,725,615 | A | * | 2/1988 | Coates et al. ............... 514/397 |
| 5,032,606 | A | * | 7/1991 | Beck et al. .................. 514/381 |
| 5,202,343 | A | * | 4/1993 | Coates et al. ............... 514/397 |
| 5,478,949 | A | * | 12/1995 | Bod et al. ................. 548/311.4 |
| 6,388,091 | B1 | * | 5/2002 | Lee et al. ................. 548/311.4 |
| 7,015,333 | B2 | * | 3/2006 | Verbeek et al. ............ 548/311.4 |
| 7,041,834 | B2 | * | 5/2006 | Hesoun et al. ........... 548/311.4 |
| 7,098,345 | B2 | * | 8/2006 | Molnar et al. ............ 548/311.4 |
| 7,288,660 | B2 | * | 10/2007 | Gutman et al. ............ 548/311.4 |
| 7,547,791 | B2 | * | 6/2009 | Kumar et al. ............. 548/335.1 |
| 2002/0115707 | A1 | * | 8/2002 | Lidor-Hadas et al. ....... 514/411 |
| 2007/0129414 | A1 | * | 6/2007 | Lee et al. ..................... 514/397 |
| 2008/0009635 | A1 | * | 1/2008 | Kumar et al. ............ 548/311.4 |

FOREIGN PATENT DOCUMENTS

| GB | 2398071 | * | 8/2004 |
| WO | WO 2002/055492 A2 | | 7/2002 |
| WO | WO 2005/037823 | * | 4/2005 |

OTHER PUBLICATIONS

Kim, et al "Heterocycles" 1997, 45: 2041.
Wagh, AP, et al "Used in complex tetralone derivatives" (Ind. J. Chem.) 1974, 12: 923.
Gras, J-L, "A direct synthesis of methylene ketones" (Tetrahedron letter) 1978, 24: 2111-2114.
Thierry, M., et al Improtance of the amide bond of Thiorphan in the inhibitor enkephalinase docking process . . . (Bioorg. Med. Chem. Lett.) 1992, 2: 949-954.
Pelletier, et al "An alumina catalyzed addition of secondary amines to exocyclic" (Tetrahedron letter) 1980, 21: 809-812.

* cited by examiner

*Primary Examiner*—Fiona T Powers
(74) *Attorney, Agent, or Firm*—Venable LLP; Keith G. Haddaway; Zayd Alathari

(57) ABSTRACT

The present invention provides a rapid, high-yielding process for preparing 1,2,3,9-tetrahydro-9-methyl-3-methylene-4H-carbazol-4-one from 1,2,3,9-tetrahydro-9-methyl-4H-carbazol-4-one without using a secondary amine as a catalyst, and without using glacial acetic acid as a solvent. The present invention further provides a rapid, high-yielding process for preparing ondansetron from 1,2,3,9-tetrahydro-9-methyl-3-methylene-4H-carbazol-4-one without using alumina as a catalyst.

31 Claims, No Drawings

PROCESS FOR PREPARING 1,2,3,9-TETRAHYDRO-9-METHYL-3-METHYLENE-4H-CARBAZOL-4-ONE AND ONDANSETRON THEREFROM

CROSS REFERENCE TO RELATED APPLICATIONS

This application claims the benefit under 35 U.S.C. §1.119 (e) of Provisional Application Ser. No. 60/602,141 filed Aug. 17, 2004.

FIELD OF THE INVENTION

The present invention provides a process for preparing 1,2,3,9-tetrahydro-9-methyl-3-methylene-4H-carbazol-4-one and a process for preparing ondansetron therefrom.

BACKGROUND OF THE INVENTION

Ondansetron (1,2,3,9-tetrahydro-9-methyl-3-[(2-methyl-1H-imidazol-1-yl)methyl]-4H-carbazol-4-one) and its polymorph (ondansetron hydrochloride dihydrate) are selective inhibitors of the serotonin 5-$HT_3$ receptor type, and are marketed for the treatment of nausea under the tradenames ZOFRAN ODT® and ZOFRAN®, respectively (GlaxoSmithKline, Research Triangle Park, N.C.).

A number of synthetic pathways for ondansetron have been reported, which involve the use of undesirable reactants or require multiple steps and undue length of time. WO 02/055492 A2 (the '492 application) discloses a process of using 1,2,3,9-tetrahydro-9-methyl-4H-carbazol-4-one as an initial substrate to prepare dimethylamino-methyl carbazolone, which is then converted to ondansetron. The '492 application process involves the use of dimethylamine, a chemical weapons precursor, as a reactant, and glacial acetic acid, a corrosive solvent, in a reaction that requires heating for 12 hours. U.S. Pat. No. 4,695,578 (the '578 patent) discloses a process of reacting 1,2,3,9-tetrahydro-9-methyl-4H-carbazol-4-one with a source of formaldehyde and dimethylamine to prepare 3-[(dimethylamino)methyl]-1,2,3,9-tetrahydro-9-methyl-4H-carbazole-4-one hydrochloride, which is then converted via multiple steps to form ondansetron. Because dimethylamine is a precursor to the nerve agent Tabun, it is a controlled substance in many countries.

Kim et al. (*Heterocycles* 1997, 45, 2041) disclose a two-step synthesis of ondansetron. In the first step of the synthesis, 1,2,3,9-tetrahydro-9-methyl-4H-carbazol-4-one (compound of formula 1, Scheme 1) is reacted with a source of formaldehyde and morpholine in boiling glacial acetic acid to provide 1,2,3,9-tetrahydro-9-methyl-3-methylene-4H-carbazol-4-one (compound of formula 2, Scheme 1). In the second step of the synthesis, 1,2,3,9-tetrahydro-9-methyl-3-methylene-4H-carbazol-4-one is reacted with 2-methylimidazole in the presence of alumina ($Al_2O_3$) to provide ondansetron (See, Scheme 1).

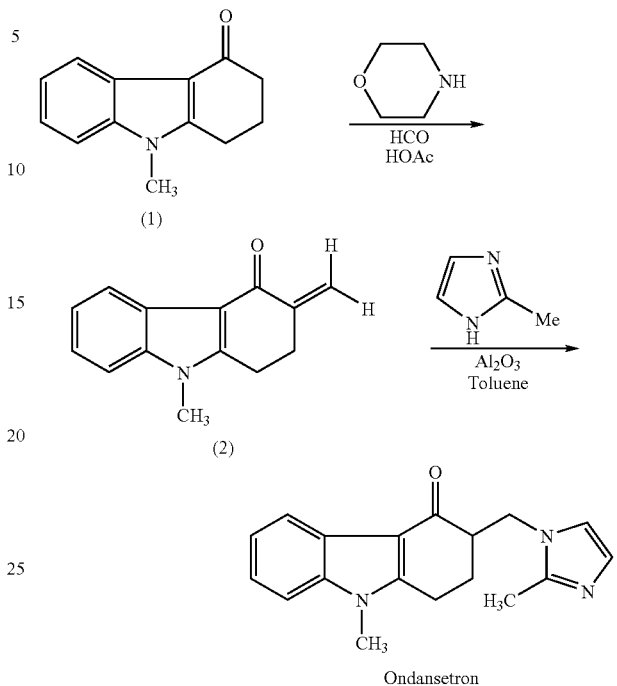

In the first step of the Kim et al. synthesis, an α-methylene group is added to 1,2,3,9-tetrahydro-9-methyl-4H-carbazol-4-one in a Mannich-related reaction. The success of the Mannich-related reaction appears to depend on the structure of the ketone substrate. Kim et al. explicitly state that reactants that are successful in other Mannich-related reactions are unsatisfactory for 1,2,3,9-tetrahydro-9-methyl-4H-carbazol-4-one. For example, formaldehyde/NaOH (used in complex tetralone derivatives; Wagh, A. P. et al., *Ind. J. Chem.,* 1974, 12, 923); trioxane/N-methylanilinium trifluoroacetate in tetrahydrofuran or dioxane (used in cyclic ketones; Gras, J-L, *Tetrahedron Lett.,* 1978, 2111); and formaldehyde/diethylamine (used in thiorphan analogs; Thierry, M. et al., *Bioorg. Med. Chem. Lett.,* 1992, 2, 949) are not suitable to add an α-methylene group to 1,2,3,9-tetrahydro-9-methyl-4H-carbazol-4-one.

In the second step of the Kim et al. synthesis, ondansetron is prepared by conjugate (Michael) addition of 2-methylimidazole to the exocyclic methylene group of 1,2,3,9-tetrahydro-9-methyl-3-methylene-4H-carbazol-4-one. Pelletier et al. (*Tetrahedron Lett.* 1980, 21, 809) explicitly state that this type of reaction generally does not occur, or takes place in low yield after a long reaction time in the absence of alumina. U.S. Pat. No. 4,695,578 discloses that when applied to the synthesis of ondansetron, the reaction in the absence of alumina takes place in low yield after a long reaction time (i.e., 43%, 20 hours).

The two-step synthesis of ondansetron disclosed by Kim et al. also suffers several major disadvantages. First, glacial acetic acid is combustible, caustic, corrosive, and extremely destructive to the tissue of mucous membranes and upper respiratory tracts. Second, glacial acetic acid is heated to its boiling point (≧115° C.), a temperature far exceeding its flash point (40° C.). Third, morpholine is flammable, corrosive, and toxic. It is readily absorbed through human skin, and is harmful by inhalation, skin contact, and ingestion. Fourth, the 1,2,3,9-tetrahydro-9-methyl-3-methylene-4H-carbazol-4-one is isolated after the first step by removing the glacial acetic acid and morpholine under vacuum, which is time-consuming and expensive. Fifth, alumina adds to the expense of the process. Sixth, the alumina contaminates the isolated ondansetron, and thus must be removed by extracting the mixture with chloroform, which is a halogenated solvent, and is undesirable commercially.

A need exists for: i) a process for preparing 1,2,3,9-tetrahydro-9-methyl-3-methylene-4H-carbazol-4-one from 1,2,3,9-tetrahydro-9-methyl-4H-carbazol-4-one without employing glacial acetic acid as a solvent or a secondary amine (e.g., dimethylamine or morpholine) as a catalyst; and ii) a process for preparing ondansetron from the 1,2,3,9-tetrahydro-9-methyl-3-methylene-4H-carbazol-4-one without employing alumina as a catalyst.

SUMMARY OF THE INVENTION

We have found that 1,2,3,9-tetrahydro-9-methyl-3-methylene-4H-carbazol-4-one can be prepared from 1,2,3,9-tetrahydro-9-methyl-4H-carbazol-4-one without using a secondary amine as a catalyst, and without using glacial acetic acid as a solvent. We have also found that ondansetron can be prepared from 1,2,3,9-tetrahydro-9-methyl-3-methylene-4H-carbazol-4-one without using alumina as a catalyst.

Accordingly, the present invention provides a process for preparing 1,2,3,9-tetrahydro-9-methyl-3-methylene-4H-carbazol-4-one, comprising the steps of:
  (a) preparing a mixture of 1,2,3,9-tetrahydro-9-methyl-4H-carbazol-4-one, a formaldehyde reagent, and a mineral acid in an aprotic solvent;
  (b) heating the mixture for about 1 hour to about 8 hours to provide 1,2,3,9-tetrahydro-9-methyl-3-methylene-4H-carbazol-4-one; and
  (c) isolating the 1,2,3,9-tetrahydro-9-methyl-3-methylene-4H-carbazol-4-one.

In one embodiment, the process provides the isolated 1,2,3,9-tetrahydro-9-methyl-3-methylene-4H-carbazol-4-one at a yield of greater than about 60%.

Preferably, the formaldehyde reagent is at least one compound selected from the group consisting of formaldehyde, paraformaldehyde, and 1,3,5-trioxane. More preferably, the formaldehyde reagent is paraformaldehyde.

Preferably, the mineral acid is at least one compound selected from the group consisting of sulfuric acid, nitric acid, phosphoric acid, perchloric acid and hydrochloric acid. More preferably, the mineral acid is hydrochloric acid.

Preferably, the aprotic solvent is a polar aprotic solvent. Preferably, the polar aprotic solvent is at least one compound selected from the group consisting of N,N-dimethylformamide (DMF), N,N-dimethylacetamide (DMA), dimethylsulfoxide (DMSO), hexamethylphosphoramide, and 1,2-dimethoxyethane (DME). More preferably, the polar aprotic solvent is N,N-dimethylformamide.

Preferably, the heating step is performed at a temperature of about 60° C. to about the reflux temperature of the mixture. More preferably, the heating step is performed at about the reflux temperature of the mixture. More preferably, the heating step is performed at about 120° C.

Preferably, the heating step is performed for about 2 hours to about 6 hours. More preferably, the heating step is performed for about 3 hours to about 5 hours.

Preferably, the isolating step is performed by filtration.

Preferably, the present process provides the isolated 1,2,3,9-tetrahydro-9-methyl-4H-carbazol-4-one at a yield of greater than about 70%.

Preferably, the mixture further comprises an ammonium salt. Preferably, the ammonium salt is an ammonium halide. More preferably, the ammonium salt is ammonium chloride.

The present invention further provides a process for preparing ondansetron, comprising the steps of:
  (a) preparing a mixture of 1,2,3,9-tetrahydro-9-methyl-3-methylene-4H-carbazol-4-one and 2-methylimidazole in toluene, with the proviso that the mixture does not contain alumina;
  (b) heating the mixture for about 1 hour to about 8 hours to provide ondansetron; and
  (c) isolating the ondansetron.

In one embodiment, the process provides the isolated ondansetron at a yield of greater than about 55%.

Preferably, the present process further comprises the steps of:
  (d) crystallizing the isolated ondansetron from a solution that comprises hydrochloric acid and water to provide ondansetron hydrochloride dihydrate; and
  (e) isolating the crystallized ondansetron hydrochloride dihydrate.

The present invention further provides a process for preparing ondansetron, comprising the steps of:
  (a) preparing a first mixture of 1,2,3,9-tetrahydro-9-methyl-4H-carbazol-4-one, a formaldehyde reagent, and a mineral acid in an aprotic solvent;
  (b) heating the first mixture for about 1 hour to about 8 hours to provide 1,2,3,9-tetrahydro-9-methyl-3-methylene-4H-carbazol-4-one;
  (c) isolating the 1,2,3,9-tetrahydro-9-methyl-3-methylene-4H-carbazol-4-one;
  (d) preparing a second mixture of the isolated 1,2,3,9-tetrahydro-9-methyl-3-methylene-4H-carbazol-4-one and 2-methylimidazole in toluene, with the proviso that the second mixture does not contain alumina;
  (e) heating the second mixture for about 1 hour to about 8 hours to provide ondansetron; and
  (f) isolating the ondansetron.

Preferably, the present process further comprises the steps of:
  (g) crystallizing the isolated ondansetron from a solution that comprises hydrochloric acid and water to provide ondansetron hydrochloride dihydrate; and
  (h) isolating the crystallized ondansetron hydrochloride dihydrate.

DETAILED DESCRIPTION OF THE INVENTION

Definitions

"Mannich reaction" refers to a reaction between a ketone, a formaldehyde reagent, and a secondary amine to provide a corresponding α-aminomethyl ketone; "Mannich-related reaction" refers to the reaction between a ketone and a formaldehyde reagent, and optionally another compound other than a secondary amine, to provide a corresponding α-methyl ketone (the methyl group may be substituted) and/or a corresponding α-methylene ketone; "heating" refers to adding thermal energy to a reaction mixture to raise the temperature of the reaction mixture above the temperature of its surrounding environment (i.e., above ambient temperature, which is typically about 22° C.); "formaldehyde reagent" refers to a molecule that is capable of donating a methylene unit ($=CH_2$) to a carbon anion; "mineral acid" refers to an inorganic acid; "aprotic solvent" refers to an organic solvent whose component molecules are not hydrogen bond donors; "polar aprotic solvent" refers to an aprotic solvent whose component molecules exhibit a molecular dipole moment; "ammonium salt" refers to a compound of formula $NH_4^+X^-$, wherein $X^-$ is the conjugate base of an acid, HX; "conjugate base" refers to a molecule that can be described as an acid that has lost one proton; "ammonium halide" refers to a compound of formula $NH_4^+X^-$, wherein $X^-$ is a halogen atom anion (i.e., $F^-$, $Cl^-$, $Br^-$, $I^-$, or $At^-$); "substantially complete" refers to a reaction that has progressed to the point where further reaction does not increase the yield of the desired product by more than about 5%; "isolating" refers to separating a crude product from a reaction mixture; "crude product" refers to a reaction product that has been separated from the reaction, but not further purified; according the present invention, a "crude product" typically has a purity of at least about 80%; "purity" refers to the percentage by weight of the major component of a mixture; "purifying" refers to increasing the purity of a compound; "crystallizing" refers to inducing crystals to form in a solution.

In a first embodiment, the present invention provides a process of preparing 1,2,3,9-tetrahydro-9-methyl-3-methylene-4H-carbazol-4-one (an intermediate for ondansetron synthesis) from 1,2,3,9-tetrahydro-9-methyl-4H-carbazol-4-one (a compound of formula 1, Scheme 2) in a Mannich-related reaction. Specifically, the present invention provides a process for preparing 1,2,3,9-tetrahydro-9-methyl-3-methylene-4H-carbazol-4-one (a compound of formula 2, Scheme 2), comprising the steps of:

(a) preparing a mixture of 1,2,3,9-tetrahydro-9-methyl-4H-carbazol-4-one, a formaldehyde reagent, and a mineral acid in an aprotic solvent;

(b) heating the mixture for about 1 hour to about 8 hours to provide 1,2,3,9-tetrahydro-9-methyl-3-methylene-4H-carbazol-4-one; and (c) isolating the 1,2,3,9-tetrahydro-9-methyl-3-methylene-4H-carbazol-4-one.

Scheme 2

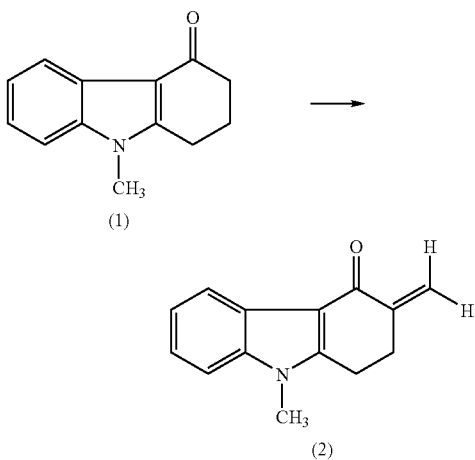

In one embodiment, the process provides the isolated 1,2,3,9-tetrahydro-9-methyl-3-methylene-4H-carbazol-4-one at a yield of greater than about 60%.

The starting material (i.e., 1,2,3,9-tetrahydro-9-methyl-4H-carbazol-4-one, a compound of formula 1) is readily available from commercial sources, such as Ningbo Pharmaceutical Co. (Zhejiang Province, China). Alternatively, the starting material can be easily prepared in accordance with the published protocol set forth in U.S. Pat. No. 4,695,578, the content of which is incorporated herein by reference in its entirety.

The formaldehyde reagent used in the present invention includes formaldehyde and other compounds that can donate a methylene unit ($=CH_2$) in a Mannich-related reaction. Formaldehyde reagents include, but are not limited to, paraformaldehyde and 1,3,5-trioxane. Preferably, the formaldehyde reagent is paraformaldehyde. Many formaldehyde reagents are available commercially, such as from Sigma-Aldrich Corp. (St. Louis, Mo.).

The formaldehyde reagent may be used in any suitable amount. For example, the formaldehyde reagent may be used in an amount of at least about 1 mole per mole of 1,2,3,9-tetrahydro-9-methyl-4H-carbazol-4-one. Preferably, the formaldehyde reagent is used in an amount of about 1 mole to about 10 moles per mole of 1,2,3,9-tetrahydro-9-methyl-4H-carbazol-4-one. More preferably, the formaldehyde reagent is used in an amount of about 2 moles to about 6 moles per mole of 1,2,3,9-tetrahydro-9-methyl-4H-carbazol-4-one. For the purpose of this invention, the amount of a formaldehyde reagent having the formula $(CH_2O)_n$ (e.g., paraformaldehyde and 1,3,5-trioxane) used in the present invention is defined with reference to the mole amount of $CH_2O$ in the formaldehyde reagent. By way of example, 1,3,5-trioxane has the formula $(CH_2O)_3$. Therefore, there are 3 moles of $CH_2O$ in each mole of 1,3,5-trioxane.

The mineral acid used in the present invention is an inorganic acid. Mineral acids include, but are not limited to, inorganic acids such as sulfuric acid, nitric acid, phosphoric acid, perchloric acid, and hydrochloric acid. Preferably, the mineral acid is hydrochloric acid.

The mineral acid may be used in any suitable amount. For example, the mineral acid may be used in an amount of at least about 0.1 mole per mole of 1,2,3,9-tetrahydro-9-methyl-4H-carbazol-4-one. Preferably, the mineral acid is used in an amount of about 0.1 mole to about 0.9 mole per mole of 1,2,3,9-tetrahydro-9-methyl-4H-carbazol-4-one. More preferably, the mineral acid is used in an amount of about 0.1 mole to about 0.5 mole per mole of 1,2,3,9-tetrahydro-9-methyl-4H-carbazol-4-one. More preferably, the mineral acid is used in an amount of about 0.25 mole per mole of 1,2,3,9-tetrahydro-9-methyl-4H-carbazol-4-one.

The aprotic solvent used in the present invention should not form covalent bonds with itself or other components of the mixture. Aprotic solvents include, but are not limited to, polar aprotic solvents. Polar aprotic solvents include, but are not limited to, N,N-dimethylformamide (DMF), N,N-dimethylacetamide (DMA), dimethylsulfoxide (DMSO), hexamethylphosphoramide, and 1,2-dimethoxyethane (DME). Preferably, the polar aprotic solvent is at least one solvent selected from the group consisting of DMF and DMA. More preferably, the polar aprotic solvent is DMF.

A mixture of 1,2,3,9-tetrahydro-9-methyl-4H-carbazol-4-one, a formaldehyde reagent, and a mineral acid in an aprotic solvent may be conveniently prepared by adding 1,2,3,9-tetrahydro-9-methyl-4H-carbazol-4-one, a formaldehyde reagent, and a mineral acid to an aprotic solvent. The sequential order in which the 1,2,3,9-tetrahydro-9-methyl-4H-carbazol-4-one, formaldehyde reagent and mineral acid are combined in an aprotic solvent is not critical.

The mixture is heated to accelerate the production of 1,2,3,9-tetrahydro-9-methyl-3-methylene-4H-carbazol-4-one from 1,2,3,9-tetrahydro-9-methyl-4H-carbazol-4-one. Preferably, the mixture is heated at a temperature of about 60° C. to about the reflux temperature of the mixture. More preferably, the mixture is heated at a temperature of about the reflux temperature of the mixture. More preferably, the mixture is heated at a temperature of about 120° C.

The heating step is performed to accelerate the Mannich-related reaction (i.e., production of 1,2,3,9-tetrahydro-9-methyl-3-methylene-4H-carbazol-4-one). Therefore, when the Mannich-related reaction is substantially complete (i.e., the production of the desired product, 1,2,3,9-tetrahydro-9-methyl-3-methylene-4H-carbazol-4-one, has slowed to the point where further heating does not increase the yield by more than about 5%), further heating is not necessary. Thin-layer chromatography (TLC) may be conveniently used to estimate the time at which the Mannich-related reaction is substantially complete.

Preferably, the Mannich-related reaction is substantially complete in about 1 hour to about 8 hours. More preferably, the reaction is substantially complete in about 2 hours to about 6 hours. More preferably, the reaction is substantially complete in about 3 hours to about 5 hours. Accordingly, the heating step is performed for about 1 hour to about 8 hours. Preferably, the heating step is performed for about 2 hours to about 6 hours. More preferably, the heating step is performed for about 3 hours to about 5 hours.

Conventional methods may be used to isolate the reaction product (i.e., 1,2,3,9-tetrahydro-9-methyl-3-methylene-4H-carbazol-4-one). Such isolation methods include, but are not limited to, filtration. The product of the Mannich-related reaction, 1,2,3,9-tetrahydro-9-methyl-3-methylene-4H-carbazol-4-one, is present in the aprotic solvent, and may be partially dissolved. Dissolved 1,2,3,9-tetrahydro-9-methyl-3-methylene-4H-carbazol-4-one may be conveniently precipitated prior to filtration. Precipitating methods include, but are not limited to, adding one or more volumes of water to the aprotic solvent. Preferably, ice water is added to the aprotic solvent. The present invention therefore provides a much simplified and improved isolation method as compared to that described by Kim et al., which requires tedious and costly steps of removing under vacuum both the solvent (i.e., glacial acetic acid, boiling point=118° C.) and the catalyst (i.e., morpholine, boiling point=129° C.).

The present invention provides a Mannich-related reaction such that 1,2,3,9-tetrahydro-9-methyl-3-methylene-4H-carbazol-4-one can be prepared at a yield of greater than about 60%. Preferably, the process of the present invention provides 1,2,3,9-tetrahydro-9-methyl-3-methylene-4H-carbazol-4-one at a yield of greater than about 70%. For the purposes of this invention, the yield may be determined according to the following formula:

Yield=(moles of 1,2,3,9-tetrahydro-9-methyl-3-methylene-4H-carbazol-4-one isolated/moles of 1,2,3,9-tetrahydro-9-methyl-4H-carbazol-4-one)×100%, wherein moles of 1,2,3,9-tetrahydro-9-methyl-3-methylene-4H-carbazol-4-one isolated=(grams of 1,2,3,9-tetrahydro-9-methyl-3-methylene-4H-carbazol-4-one isolated)/(211 grams/mole); and moles of 1,2,3,9-tetrahydro-9-methyl-4H-carbazol-4-one=(grams of 1,2,3,9-tetrahydro-9-methyl-4H-carbazol-4-one used in step (a))/(199 grams/mole)

Accordingly, the present invention provides an improved process for preparing 1,2,3,9-tetrahydro-9-methyl-3-methylene-4H-carbazol-4-one from 1,2,3,9-tetrahydro-9-methyl-4H-carbazol-4-one. There are many advantages of the present invention, which are unforeseen and surprising.

An advantage of the present invention is that the present disclosed process does not require the use of a hazardous solvent. In contrast, many prior art processes (e.g., Kim et al. and WO 02/055492) require the use of glacial acetic acid as a solvent that is heated to a temperature more than 70° C., higher than its flash point.

Another advantage of the present invention is that the present disclosed process does not necessarily require a secondary amine. Secondary amines are almost always used in a Mannich reaction. Many of the secondary amines (e.g., dimethylamine and morpholine) are disadvantageous for commercial uses. However, the presence of a secondary amine in the presently claimed process is not detrimental to the reaction. Preferably, the present invention does not include a secondary amine.

Another advantage of the present invention is that the present disclosed process provides 1,2,3,9-tetrahydro-9-methyl-3-methylene-4H-carbazol-4-one in high yield after a short reaction time. In contrast, other Mannich-related processes are not suitable for the preparation of 1,2,3,9-tetrahydro-9-methyl-3-methylene-4H-carbazol-4-one (Kim et al., *Heterocycles* 1997, 45, 2041).

Another advantage of the present invention is that the present disclosed process permits efficient and convenient isolation of the 1,2,3,9-tetrahydro-9-methyl-3-methylene-4H-carbazol-4-one. In contrast, the Kim et al. process requires large volumes of glacial acetic acid to be removed under vacuum, which is commercially impracticable.

Another further advantage of the present invention is that the isolated 1,2,3,9-tetrahydro-9-methyl-3-methylene-4H-carbazol-4-one can be used to prepare ondansetron without further purification. However, the isolated 1,2,3,9-tetrahydro-9-methyl-3-methylene-4H-carbazol-4-one may be further purified, only if desired. Suitable purification methods include, but are not limited to, conventional protocol such as chromatography and crystallization.

Optionally, the Mannich-related reaction in the present invention may further include an ammonium salt. Without wishing to be bound by any theory, it is believed that the ammonium salt may act as a catalyst in the Mannich-related reaction. The ammonium salt used in the present invention may be obtained from a commercial source, such as from Sigma-Aldrich Corp. (St. Louis, Mo.). Alternatively, the ammonium salt may be chemically prepared. For example, ammonia can be reacted with hydrochloric acid to prepare ammonium chloride.

Optionally, the ammonium salt can be prepared in situ during the step (a) of the presently claimed process. For example, ammonia and an acid (e.g., hydrochloric acid) can be added to the aprotic solvent during the step (a) of the process to generate the ammonium salt. Suitable ammonium salts include, but are not limited to, ammonium halides (e.g., ammonium bromide, ammonium chloride, ammonium fluoride, and ammonium iodide). Preferably, the ammonium salt is an ammonium halide. More preferably, the ammonium salt is ammonium chloride.

The ammonium salt may be used in any suitable amount. For example, the ammonium salt may be used in an amount of at least about 0.1 mole per mole of 1,2,3,9-tetrahydro-9-methyl-4H-carbazol-4-one. Preferably, the ammonium salt is used in an amount of about 0.1 mole to about 1 mole per mole of 1,2,3,9-tetrahydro-9-methyl-4H-carbazol-4-one. More preferably, the ammonium salt is used in an amount of about 0.5 mole to about 1 mole per mole of 1,2,3,9-tetrahydro-9-methyl-4H-carbazol-4-one. More preferably, the ammonium salt is used in an amount of about 0.9 mole per mole of 1,2,3,9-tetrahydro-9-methyl-4H-carbazol-4-one.

Optionally, the isolated 1,2,3,9-tetrahydro-9-methyl-3-methylene-4H-carbazol-4-one may be further converted to form ondansetron. It is to be understood that the present first embodiment may be combined with a conventional protocol to convert the prepared 1,2,3,9-tetrahydro-9-methyl-3-methylene-4H-carbazol-4-one to ondansetron. Conventional protocols of converting 1,2,3,9-tetrahydro-9-methyl-3-methylene-4H-carbazol-4-one to ondansetron are exemplified in U.S. Pat. No. 4,695,578 and Kim et al., the contents of which are incorporated by reference. Hence, the present invention provides a process for preparing ondansetron starting from 1,2,3,9-tetrahydro-9-methyl-4H-carbazol-4-one, comprising the steps of:

(a) preparing a mixture of 1,2,3,9-tetrahydro-9-methyl-4H-carbazol-4-one, a formaldehyde reagent, and a mineral acid in an aprotic solvent;

(b) heating the mixture for about 1 hour to about 8 hours to provide 1,2,3,9-tetrahydro-9-methyl-3-methylene-4H-carbazol-4-one;

(c) isolating the 1,2,3,9-tetrahydro-9-methyl-3-methylene-4H-carbazol-4-one; and (d) converting the isolated 1,2,3,9-tetrahydro-9-methyl-3-methylene-4H-carbazol-4-one to form ondansetron.

In a second embodiment, the present invention provides a process for converting 1,2,3,9-tetrahydro-9-methyl-3-methylene-4H-carbazol-4-one (a compound of formula 2) to form ondansetron (See, Scheme 3). Specifically, the present invention provides a process for preparing ondansetron, comprising the steps of:

(a) preparing a mixture of 1,2,3,9-tetrahydro-9-methyl-3-methylene-4H-carbazol-4-one and 2-methylimidazole in toluene, with the proviso that the mixture does not contain alumina;

(b) heating the mixture for about 1 hour to about 8 hours to provide ondansetron; and (c) isolating the ondansetron.

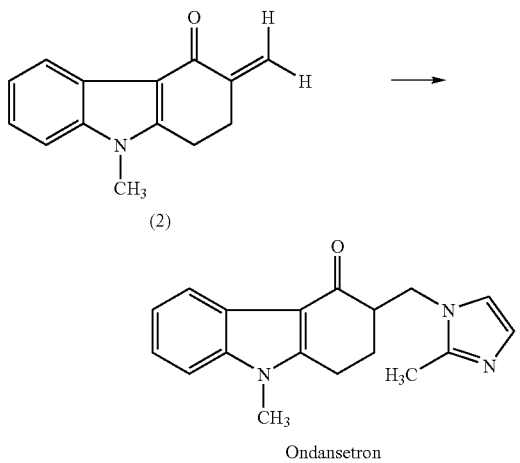

Scheme 3

(2)

Ondansetron

In one embodiment, the process provides the isolated ondansetron at a yield of greater than about 55%.

It is to be understood that the 1,2,3,9-tetrahydro-9-methyl-3-methylene-4H-carbazol-4-one prepared by a standard protocol may be combined with the presently claimed second embodiment to form ondansetron. The starting material, 1,2,3,9-tetrahydro-9-methyl-3-methylene-4H-carbazol-4-one, may be conveniently prepared using a standard protocol as disclosed in Kim et al. and U.S. Pat. No. 4,695,578.

Preferably, 1,2,3,9-tetrahydro-9-methyl-3-methylene-4H-carbazol-4-one is prepared using the process as described above; that is, heating a mixture containing 1,2,3,9-tetrahydro-9-methyl-4H-carbazol-4-one, a formaldehyde reagent, and a mineral acid in an aprotic solvent for about 1 hour to about 8 hours to prepare 1,2,3,9-tetrahydro-9-methyl-3-methylene-4H-carbazol-4-one.

The 2-methylimidazole may be used in any suitable amount. For example, the 2-methylimidazole is used in an amount of at least about 1 mole per mole of 1,2,3,9-tetrahydro-9-methyl-3-methylene-4H-carbazol-4-one. Preferably, the 2-methylimidazole is used in an amount of about 1 mole to about 5 moles per mole of 1,2,3,9-tetrahydro-9-methyl-3-methylene-4H-carbazol-4-one. More preferably, the 2-methylimidazole is used in an amount of about 1 mole to about 3 moles per mole of 1,2,3,9-tetrahydro-9-methyl-3-methylene-4H-carbazol-4-one.

A mixture of 1,2,3,9-tetrahydro-9-methyl-3-methylene-4H-carbazol-4-one and 2-methylimidazole in toluene may be conveniently prepared by adding 1,2,3,9-tetrahydro-9-methyl-3-methylene-4H-carbazol-4-one and 2-methylimidazole to toluene. The sequential order in which the 1,2,3,9-tetrahydro-9-methyl-3-methylene-4H-carbazol-4-one, 2-methylimidazole, and toluene are combined is not critical.

The mixture (i.e., 1,2,3,9-tetrahydro-9-methyl-3-methylene-4H-carbazol-4-one and 2-methylimidazole in toluene) is heated to accelerate the production of ondansetron from 1,2,3,9-tetrahydro-9-methyl-3-methylene-4H-carbazol-4-one. Preferably, the mixture is heated at a temperature of about 50° C. to about the reflux temperature of the mixture. More preferably, the mixture is heated at a temperature of about the reflux temperature of the mixture. More preferably, the mixture is heated at a temperature of about 110° C.

The heating step is performed for a time duration such that the reaction is substantially complete (i.e., the production of the desired product (i.e., ondansetron) has slowed to the point where further heating does not increase the yield by more than about 5%). After the reaction is substantially complete, further heating is not necessary. Thin-layer chromatography (TLC) may be conveniently used to estimate the time duration at which the reaction is substantially complete.

Preferably, the Mannich-related reaction is substantially complete in about 1 hour to about 8 hours. More preferably, the reaction is substantially complete in about 1 hour to about 5 hours. More preferably, the reaction is substantially complete in about 2 hours to about 4 hours. Accordingly, the heating step is performed for about 1 hour to about 8 hours. More preferably, the heating step is performed for about 1 hour to about 5 hours. More preferably, the heating step is performed for about 2 hours to about 4 hours.

Conventional methods may be used to isolate the resulting product (i.e., ondansetron) after the heating step. Such isolation methods include, but not limited to, precipitation followed by filtration. The precipitation may further be enhanced by cooling. Thus, the present invention provides a substantially improved isolation method over that of Kim et al., which requires multiple steps (including the use of chloroform) to isolate the ondansetron from the alumina.

In accordance with the present invention, the conversion of 1,2,3,9-tetrahydro-9-methyl-3-methylene-4H-carbazol-4-one to ondansetron has a yield of greater than about 55%. Preferably, the present invention provides a yield of greater than about 70%. More preferably, the present invention provides a yield of greater than about 90%. For the purposes of this invention, the yield may be determined according to the following formula:

Yield=(moles of ondansetron isolated/moles of 1,2,3, 9-tetrahydro-9-methyl-3-methylene-4H-carbazol-4-one)×100%, wherein moles of ondansetron isolated=(grams of ondansetron isolated)/(293 grams/mole); and moles of 1,2,3,9-tetrahydro-9-methyl-3-methylene-4H-carbazol-4-one=(grams of 1,2,3,9-tetrahydro-9-methyl-3-methylene-4H-carbazol-4-one used in step (a))/(211 grams/mole)

Accordingly, the present invention provides an improved process for preparing ondansetron from 1,2,3,9-tetrahydro-9-methyl-3-methylene-4H-carbazol-4-one. There are many advantages of the present invention, which are unforeseen and surprising.

An advantage of the present invention is that the present disclosed process (converting 1,2,3,9-tetrahydro-9-methyl-3-methylene-4H-carbazol-4-one to ondansetron) does not require the use of alumina. Pelletier et al. and Kim et al. emphasize the essential role of alumina in this conversion process. The finding that the conversion reaction can proceed without the use of alumina (while maintaining high yields) is surprising and significantly simplifies the reaction process and reduces cost expense in commercial production.

Another advantage of the present invention is that the present disclosed process permits the ondansetron to be isolated by filtration, which overcomes the problem of extracting an alumina/ondansetron mixture with chloroform, which is tedious and commercially undesirable. In contrast, the process of Kim et al. requires separation of alumina from ondansetron.

Another further advantage of the present invention is that the present disclosed process provides ondansetron at a high yield in a short reaction time. The conversion of 1,2,3,9-tetrahydro-9-methyl-3-methylene-4H-carbazol-4-one to ondansetron involves adding a secondary amine to an exocyclic α,β-unsaturated ketone, which is known to be a difficult reaction (See, Pelletier et al.). The present invention provides an easy reaction process for preparing ondansetron (without the use of alumina) and is therefore, superior to that of those disclosed by Pelletier et al. and Kim et al.

Optionally, the prepared ondansetron may be further purified to using standard methods. Convenient methods include, but not limited to, chromatography and crystallization.

Preparation of Ondansetron Hydrochloride Dihydrate

Optionally, the prepared ondansetron may be further converted to form ondansetron hydrochloride dihydrate. It is to be understood that the present first and second embodiments may be combined with a convention protocol to convert the prepared ondansetron to ondansetron hydrochloride dihydrate. Conventional crystallization processes for preparing ondansetron hydrochloride dihydrate include, but not limited to, U.S. Pat. No. 4,695,578, the content of which is incorporated by reference.

Hence, the present invention provides a process for preparing ondansetron hydrochloride dihydrate starting from 1,2,3,9-tetrahydro-9-methyl-4H-carbazol-4-one, comprising the steps of:

(a) preparing a mixture of 1,2,3,9-tetrahydro-9-methyl-4H-carbazol-4-one, a formaldehyde reagent, and a mineral acid in an aprotic solvent;
(b) heating the mixture for about 1 hour to about 8 hours to provide 1,2,3,9-tetrahydro-9-methyl-3-methylene-4H-carbazol-4-one;
(c) isolating the 1,2,3,9-tetrahydro-9-methyl-3-methylene-4H-carbazol-4-one;
(d) converting the isolated 1,2,3,9-tetrahydro-9-methyl-3-methylene-4H-carbazol-4-one to form ondansetron;
(e) isolating the ondansetron; and
(f) crystallizing the isolated ondansetron to form ondansetron hydrochloride dihydrate.

The present invention further provides a process for preparing ondansetron hydrochloride dihydrate starting from 1,2,3,9-tetrahydro-9-methyl-3-methylene-4H-carbazol-4-one, comprising the steps of:

(a) preparing a mixture of 1,2,3,9-tetrahydro-9-methyl-3-methylene-4H-carbazol-4-one and 2-methylimidazole in toluene, with the proviso that the mixture does not contain alumina;
(b) heating the mixture for about 1 hour to about 8 hours to provide ondansetron;
(c) isolating the ondansetron; and
(d) crystallizing the isolated ondansetron to form ondansetron hydrochloride dihydrate.

The present invention is illustrated, but not limited, by the following examples.

EXAMPLES

Example 1

Synthesis of 1,2,3,9-Tetrahydro-9-methyl-3-methylene-4H-carbazol-4-one (Without Using Glacial Acetic Acid or Secondary Amine)

1,2,3,9-tetrahydro-9-methyl-4H-carbazol-4-one (1.75 grams; 8.8 mmol), paraformaldehyde (1.55 grams; equivalent to about 50 mmol $CH_2O$), and 0.25 mL (2 mmol) concentrated HCl (32% (w/w)) were added to N,N-dimethylformamide (8.75 mL). The mixture was heated to 110° C.

At various time points during the reaction, samples were collected and analyzed by thin-layer chromatography (TLC). The ratio of product (1,2,3,9-tetrahydro-9-methyl-3-methylene-4H-carbazol-4-one) to starting material (1,2,3,9-tetrahydro-9-methyl-4H-carbazol-4-one) in the samples was visually estimated. The results are shown in the following table 1.

TABLE 1

| Time | Ratio of 1,2,3,9-tetrahydro-9-methyl-3-methylene-4H-carbazol-4-one to 1,2,3,9-tetrahydro-9-methyl-4H-carbazol-4-one |
| --- | --- |
| 1 hour | 50/50 |
| 2 hours | 60/40 |
| 3 hours | 70/30 |
| 4 hours | 80/20 |
| 5 hours | 85/15 |
| Overnight | 100/0* |

*only traces of 1,2,3,9-tetrahydro-9-methyl-4H-carbazol-4-one remaining

Accordingly, 1,2,3,9-tetrahydro-9-methyl-3-methylene-4H-carbazol-4-one was synthesized from 1,2,3,9-tetrahydro-9-methyl-4H-carbazol-4-one using a formaldehyde reagent (paraformaldehyde) and a mineral acid (HCl) in an aprotic solvent (DMF). Note that this reaction was rapid and high yielding, even though it was performed without using glacial acetic acid as a solvent, and without using a secondary amine as a catalyst.

Example 2

Synthesis of 1,2,3,9-Tetrahydro-9-methyl-3-methylene-4H-carbazol-4-one-(Optional Use of Ammonium Chloride)

In this reaction, we studied the optional use of ammonium chloride. The reaction was performed under conditions identical to those used in Example 1, except that ammonium chloride (0.045 grams; 0.85 mmol) was included in the reaction.

At various time points during the reaction, samples were collected and analyzed by thin-layer chromatography (TLC). The ratio of product (1,2,3,9-tetrahydro-9-methyl-3-methylene-4H-carbazol-4-one) to starting material (1,2,3,9-tetrahydro-9-methyl-4H-carbazol-4-one) in the samples was visually estimated. The results are shown in the following table 2.

TABLE 2

| Time | Ratio of 1,2,3,9-tetrahydro-9-methyl-3-methylene-4H-carbazol-4-one to 1,2,3,9-tetrahydro-9-methyl-4H-carbazol-4-one |
| --- | --- |
| 1 hour | 60/40 |
| 2 hours | 70/30 |
| 3 hours | 80/20 |
| 4 hours | 90/10 |
| 5 hours | 95/5 |
| Overnight | 100/0* |

*appeared to be no 1,2,3,9-tetrahydro-9-methyl-4H-carbazol-4-one remaining

Accordingly, 1,2,3,9-tetrahydro-9-methyl-3-methylene-4H-carbazol-4-one was synthesized from 1,2,3,9-tetrahydro-9-methyl-4H-carbazol-4-one using a formaldehyde reagent (paraformaldehyde), a mineral acid (HCl), and an ammonium salt (ammonium chloride) in an aprotic solvent (DMF). The ammonium salt appears to have had a positive impact on the rate of the reaction.

Example 3

Large Scale Synthesis and Isolation of 1,2,3,9-tetrahydro-9-methyl-3-methylene-4H-carbazol-4-one We studied large-scale synthesis by increasing the quantity of reagents by 100-fold as compared to Example 2, and isolating the product of the reaction (i.e., 1,2,3,9-tetrahydro-9-methyl-3-methylene-4H-carbazol-4-one). 1,2,3,9-tetrahydro-9-methyl-4H-carbazol-4-one (175 grams; 0.88 mol), paraformaldehyde (155 grams; equivalent to about 5 moles of $CH_2O$), ammonium chloride (45 grams; 0.84 mol), and concentrated (32% (w/w)) hydrochloric acid (25 mL; 0.2 mol) were added to N,N-dimethylformamide (875 mL).

The mixture was heated for 5-6 hours at 120° C. At this point, thin-layer chromatography (TLC) indicated complete conversion of 1,2,3,9-tetrahydro-9-methyl-4H-carbazol-4-one to 1,2,3,9-tetrahydro-9-methyl-3-methylene-4H-carbazol-4-one. The solution was cooled to room temperature (about 20-25° C.), and ice water (2 L) was added.

The resulting white precipitate was collected by filtration. The filtrate was extracted twice with toluene. The combined toluene extracts were concentrated under vacuum, and the residue was combined with the filtered product to provide 145 grams (0.69 mol; 78% yield) of crude 1,2,3,9-tetrahydro-9-methyl-3-methylene-4H-carbazol-4-one.

Accordingly, the large-scale production of 1,2,3,9-tetrahydro-9-methyl-3-methylene-4H-carbazol-4-one from 1,2,3,9-tetrahydro-9-methyl-4H-carbazol-4-one proceeded in a yield of about 78% after heating for about 5-6 hours. The 1,2,3,9-tetrahydro-9-methyl-3-methylene-4H-carbazol-4-one was isolated quickly and efficiently by simply adding ice water to the reaction mixture, and then filtering.

Example 4

Synthesis of Ondansetron without Using Alumina

In this reaction, we examined the feasibility of producing ondansetron from 1,2,3,9-tetrahydro-9-methyl-3-methylene-4H-carbazol-4-one without alumina as a catalyst. The crude 1,2,3,9-tetrahydro-9-methyl-3-methylene-4H-carbazol-4-one from Example 3 (145 grams, 0.69 mol) and 2-methylimidazole (71 grams; 0.86 mol) were added to toluene (800 mL), and the mixture was heated to reflux temperature. After about 3-4 hours (TLC indicated that 1,2,3,9-tetrahydro-9-methyl-3-methylene-4H-carbazol-4-one had been substantially consumed), the reaction was cooled to room temperature.

The resulting precipitate was isolated by filtration to provide 190 grams (0.65 mol; 94% yield) of crude ondansetron.

Accordingly, ondansetron was prepared from 1,2,3,9-tetrahydro-9-methyl-3-methylene-4H-carbazol-4-one in a yield of about 94% after heating for about 3-4 hours. Note that alumina was not used as a catalyst. In addition, the ondansetron was isolated from the reaction mixture quickly and efficiently by filtering the reaction mixture.

Example 5

Synthesis of Ondansetron Hydrochloride Dihydrate

The crude ondansetron from Example 4 (190 grams; 0.65 mol) was suspended in a mixture of isopropanol (1.2 L) and water (0.24 L). Concentrated hydrochloric acid (32% (w/w)) was added until the pH of the mixture was about 1-2 (about 70 mL). The solution was heated to reflux temperature for one hour and then cooled to room temperature. The precipitated crystals were collected by filtration, and dried to provide 117 grams (0.32 mol; 49% yield) of crude ondansetron hydrochloride dihydrate. The purity was determined to be about 98-99% by HPLC.

The crude ondansetron hydrochloride dihydrate was recrystallized from a mixture of isopropanol and water (6:1 v/v) to provide a crystalline product having a purity of at least 99.8% by HPLC.

Example 6

Synthesis of 1,2,3,9-tetrahydro-9-methyl-3-methylene-4H-carbazol-4-one using sulfuric acid 10 ml of sulfuric acid was added drop wise to 175 ml of cooled DMF (10-15° C.); the temperature of the reaction was maintained below 25° C. Thirty five gm (17.5 mmol) of Carbazolone were then introduced to the reaction mixture, followed by the addition of 13.1 gm (43.75 mmol) of paraformaldehyde. The reaction mixture was heated to 90° C. for 2 hours. The temperature of the reaction mixture was then raised to 110-115° C. and the reaction mixture stirred for an additional 2 hours. An aliquot of the reaction mixture was analyzed for the presence of starting material by high pressure liquid chromatography ("HPLC"). After no more starting material was detected, the solution was cooled to 40° C. and 300 ml of water were added to precipitate the product, 1,2,3,9-tetrahydro-9-methyl-3-methylene-4H-carbazol-4- one. The mixture was stirred about 1 hour, the product filtered and washed with water. The yield of the crude product was about 80% and the purity 92-95%. Ondansetron can then be prepared from the intermediate using the methods described herein.

Numerous references, including patents, patent applications and various publications, are cited and discussed in the description of this invention. All references cited and discussed in this specification are incorporated herein by reference in their entirety and to the same extent as if each reference was individually incorporated by reference.

What is claimed is:

1. A process for preparing 1,2,3,9-tetrahydro-9-methyl-3-methylene-4H-carbazol-4-one, comprising the steps of:
    (a) preparing a mixture of 1,2,3,9-tetrahydro-9-methyl-4H-carbazol-4-one, a formaldehyde reagent, and a mineral acid in an aprotic solvent;
    (b) heating the mixture for about 1 hour to about 8 hours to provide 1,2,3,9-tetrahydro-9-methyl-3-methylene-4H-carbazol-4-one; and
    (c) isolating the 1,2,3,9-tetrahydro-9-methyl-3-methylene-4H-carbazol-4-one;
    wherein the mixture further comprises an ammonium salt.

2. The process of claim 1, wherein the process provides the isolated 1,2,3,9-tetrahydro-9-methyl-3-methylene-4H-carbazol-4-one at a yield of greater than about 60%.

3. The process of claim 1, wherein the formaldehyde reagent is at least one compound selected from the group consisting of formaldehyde, paraformaldehyde, and 1,3,5-trioxane.

4. The process of claim 1, wherein the formaldehyde reagent is paraformaldehyde.

5. The process of claim 1, wherein the mineral acid is at least one compound selected from the group consisting of sulfuric acid, nitric acid, phosphoric acid, perchloric acid and hydrochloric acid.

6. The process of claim 1, wherein the mineral acid is sulfuric acid.

7. The process of claim 1, wherein the mineral acid is hydrochloric acid.

8. The process of claim 1, wherein the aprotic solvent is a polar aprotic solvent.

9. The process of claim 8, wherein the polar aprotic solvent is selected from the group consisting of N,N-dimethylformamide, N,N-dimethylacetamide, dimethylsulfoxide, hexamethylphosphoramide, and 1,2-dimethoxyethane.

10. The process of claim 9, wherein the polar aprotic solvent is N,N-dimethylformamide.

11. The process of claim 1, wherein the heating step is performed at a temperature of about 60° C. to about the reflux temperature of the mixture.

12. The process of claim 1, wherein the heating step is performed at the reflux temperature of the mixture.

13. The process of claim 10, wherein the heating step is performed at about 120° C.

14. The process of claim 1, wherein the heating step is performed from about 2 hours to about 6 hours.

15. The process of claim 10, wherein the heating step is performed from about 3 hours to about 5 hours.

16. The process of claim 1, wherein the isolating step is performed by filtration.

17. The process of claim 1, wherein the process provides the isolated 1,2,3,9-tetrahydro-9-methyl-3-methylene-4H-carbazol-4-one at a yield of greater than about 70%.

18. The process of claim 1, wherein the ammonium salt is an ammonium halide.

19. The process of claim 18, wherein the ammonium salt is ammonium chloride.

20. A process for preparing ondansetron, comprising the steps of
    (a) preparing a first mixture of 1,2,3,9-tetrahydro-9-methyl-4H-carbazol-4-one, a formaldehyde reagent, and a mineral acid in an aprotic solvent:
    (b) heating the first mixture for about 1 hour to about 8 hours to provide 1,2,3,9-tetrahydro-9-methy 1-3-methylene-4H-carbazol-4-one:
    (c) isolating the 1,2,3,9-tetrahydro-9-methy 1-3-methylene-4H-carbazol-4-one:
    (d) preparing a mixture of isolated 1,2,3,9-tetrahydro-9-methyl-3-methylene-4H-carbazol-4-one and 2-methylimidazole in toluene, with the proviso that the mixture does not contain alumina;
    (e) heating the mixture for about 1 hour to about 8 hours to provide ondansetron; and
    (f) isolating the ondansetron;
    wherein the first mixture does not include a secondary amine.

21. The process of claim 20, wherein the process provides the isolated ondansetron at a yield of greater than about 55%.

22. The process of claim 20, further comprising the steps of:
    (g) crystallizing the isolated ondansetron from a solution that comprises hydrochloric acid and water to provide ondansetron hydrochloride dihydrate; and
    (h) isolating the crystallized ondansetron hydrochloride dihydrate.

23. A process for preparing ondansetron, comprising the steps of:
    (a) preparing a first mixture of 1,2,3,9-tetrahydro-9-methyl-4H-carbazol-4-one, a formaldehyde reagent, and a mineral acid in an aprotic solvent;
    (b) heating the first mixture for about 1 hour to about 8 hours to provide 1,2,3,9-tetrahydro-9-methy 1-3-methylene-4H-carbazol-4-one;
    (c) isolating the 1,2,3,9-tetrahydro-9-methy 1-3-methylene-4H-carbazol-4-one;
    (d) preparing a second mixture of the isolated 1,2,3,9-tetrahydro-9-methyl-3-methylene-4H-carbazol-4-one and 2-methylimidazole in toluene, with the proviso that the second mixture does not contain alumina;
    (e) heating the second mixture for about 1 hour to about 8 hours to provide ondansetron; and
    (f) isolating the ondansetron;
    wherein the first mixture further comprises an ammonium salt.

24. The process of claim 23, further comprising the steps of:
    (g) crystallizing the isolated ondansetron from a solution that comprises hydrochloric acid and water to provide ondansetron hydrochloride dihydrate; and
    (h) isolating the crystallized ondansetron hydrochloride dihydrate.

25. The process of claim 1, wherein the mixture does not include a secondary amine.

26. A process for preparing 1,2,3,9-tetrahydro-9-methyl-3-methylene-4H-carbazol-4-one, comprising the steps of:
    (a) preparing a mixture of 1,2,3,9-tetrahydro-9-methyl-4H-carbazol-4-one, a formaldehyde reagent, and a mineral acid in an aprotic solvent;
    (b) heating the mixture for about 1 hour to about 8 hours to provide 1,2,3,9-tetrahydro-9-methyl-3-methylene-4H-carbazol-4-one; and (c) isolating the 1,2,3,9-tetrahydro-9-methyl-3-methylene-4H-carbazol-4-one;

wherein the mixture does not include a secondary amine.

27. The process of claim 26, wherein the aprotic solvent is selected from the group consisting of N,N-dimethylformamide, N,N-dimethylacetamide, dimethylsulfoxide, hexamethylphosphoramide, and 1,2-dimethoxyethane.

28. The process of claim 26, wherein the process provides the isolated 1,2,3,9-tetrahydro-9-methyl-3-methylene-4H-carbazol-4-one at a yield of greater than about 60%.

29. The process of claim 26, wherein the formaldehyde reagent is at least one compound selected from the group consisting of formaldehyde, paraformaldehyde, and 1,3,5-trioxane.

30. The process of claim 26, wherein the mineral acid is at least one compound selected from the group consisting of sulfuric acid, nitric acid, phosphoric acid, perchloric acid and hydrochloric acid.

31. The process of claim 23, wherein the process provides the isolated ondansetron at a yield of greater than about 55%.

* * * * *